(12) United States Patent
Wright et al.

(10) Patent No.: US 7,828,763 B2
(45) Date of Patent: Nov. 9, 2010

(54) MICRODIALYSIS PROBE WITH A SPIRAL LINE

(75) Inventors: Gavin Wright, Wemyss (GB); Bruno Reihl, Wilen bei Wollerau (CH); Hanspeter Heiniger, Lotzwil (CH); Ulrich Haueter, Grosshoechstetten (CH)

(73) Assignee: Roche Diagnostics International AG, Steinhausen (CH)

( * ) Notice: Subject to any disclaimer, the term of this patent is extended or adjusted under 35 U.S.C. 154(b) by 0 days.

(21) Appl. No.: 11/940,636

(22) Filed: Nov. 15, 2007

(65) Prior Publication Data

US 2008/0228131 A1 Sep. 18, 2008

Related U.S. Application Data

(63) Continuation of application No. 11/096,708, filed on Apr. 1, 2005, now abandoned, which is a continuation of application No. PCT/EP03/10534, filed on Sep. 22, 2003.

(51) Int. Cl.
*A61M 1/28* (2006.01)
(52) U.S. Cl. .......................................... 604/29; 604/44
(58) Field of Classification Search ............... 604/29, 604/44, 46; 600/366
See application file for complete search history.

(56) References Cited

U.S. PATENT DOCUMENTS

| 4,016,863 A | 4/1977 | Brantigan |
| 4,235,231 A | 11/1980 | Schindler et al. |
| 4,265,249 A | 5/1981 | Schindler et al. |
| 4,516,580 A | 5/1985 | Polanyi |
| 4,694,832 A | 9/1987 | Ungerstedt |
| 4,726,381 A | 2/1988 | Jones |
| 4,763,658 A | 8/1988 | Jones |
| 4,765,339 A | 8/1988 | Jones |
| 4,774,955 A | 10/1988 | Jones |
| 4,901,727 A | 2/1990 | Goodwin |
| 6,013,029 A | 1/2000 | Korf et al. |
| 6,272,370 B1 | 8/2001 | Gillies et al. |
| 6,561,996 B1 | 5/2003 | Gorsuch |
| 2005/0137471 A1 | 6/2005 | Haar et al. |
| 2005/0277820 A1 | 12/2005 | Wright et al. |

FOREIGN PATENT DOCUMENTS

| DE | 2734248 A1 | 2/1979 |
| DE | 2737922 A1 | 3/1979 |
| DE | 19714572 C1 | 6/1998 |
| WO | 99/59655 A1 | 11/1999 |

*Primary Examiner*—Kevin C. Sirmons
*Assistant Examiner*—Michael J Anderson
(74) *Attorney, Agent, or Firm*—Dorsey & Whitney LLP

(57) ABSTRACT

A microdialysis probe with a probe body, a probe needle for introduction into a tissue, an inlet line and an outlet line for a perfusion solution and a dialysis membrane, wherein at least one hollow channel forms the outlet line and extends at least partly spirally about the probe needle on an external surface of the probe needle. The inlet for the perfusion solution may also be in the form of spiral about the external surface of the probe needle.

5 Claims, 2 Drawing Sheets

MICRODIALYSIS PROBE WITH A SPIRAL LINE

CROSS-REFERENCE TO RELATED APPLICATION(S)

This application is a continuation of and claims priority to U.S. patent application Ser. No. 11/096,708, filed on Apr. 1, 2005, now abandoned, which is a continuation of and claims priority to International Application No. PCT/EP2003/010534, filed on Sep. 22, 2003, which claims priority to German Application No. 102 46 207.0, filed Oct. 4, 2002, the contents of which are incorporated in their entirety herein by reference.

BACKGROUND

The present invention relates to microdialysis probes, in particular a microdialysis probe for measuring the concentration of a dissolved substance in a tissue.

Microdialysis probes generally comprise a probe body and an injection needle as probe needle for introduction into, for example, a human or animal tissue, the probe needle being completely surrounded by the tissue. The probe needle comprises an inlet line (or conduit) and an outlet line for a perfusion solution. Moreover, in one area of the line for the perfusion solution, a dialysis membrane is arranged to be in contact with the tissue environment. Between the tissue environment and the perfusion solution, the concentration of permeable substances dissolved in the tissue is equalized along the membrane surface.

Conventional microdialysis probes typically have, for example, a coaxial structure. Two hollow cylinders are arranged one inside the other, the inner hollow cylinder serving as an inlet line for the perfusion solution which, at a transition area in a distal end portion of the probe needle, passes into the area between the inner cylinder and the outer cylinder and is conveyed back within this annular channel. The dialysis membrane can, for example, be arranged in a front area where the perfusion solution turns back or, alternatively, it can form part of the outer hollow cylinder. Microdialysis probes of this type have the disadvantage that the perfusion solution comes into contact with the tissue environment only across a small membrane surface and, at most, across the length of the probe needle, and that a membrane hollow fiber acting as outer cylinder is exposed to the pressure of the tissue, and the outlet line can therefore become blocked. Moreover, in the case of a short probe needle, there is often not enough time left to obtain a complete concentration equalization. By contrast, a long probe needle is unpleasant for the user. With a straight return of the perfusion solution, the flow velocity is too high to permit all of the desired concentration equalization.

DE 199 37 099 A1 discloses microdialysis probes in which the inlet line and outlet line for a perfusion solution are arranged next to one another. For this purpose, two mutually adjacent tubes, for example, are provided which have a flow transfer area for the perfusion solution. It is also possible to arrange, inside a microdialysis membrane in the form of a hollow fiber, a support structure which divides the hollow fiber into different hollow channels, again with the possibility of a flow transfer between the channels being provided. Here too, the inlet line and outlet line have a straight course, with the result that concentration equalization is, in some cases, not optimal.

SUMMARY

Objects of the present invention include providing a microdialysis probe which is comfortable for the user, is easy to produce, has a perfusion solution flow profile optimized for concentration equalization, and has an improved arrangement of the dialysis surface.

In one embodiment, the present invention comprises a microdialysis probe with a probe body and a probe needle for introduction into a tissue, said probe needle having a needle tip, an inlet line (or conduit) for a perfusion solution, an outlet line (or conduit) for the perfusion solution, and a dialysis membrane, wherein at least the outlet line comprises a hollow channel which extends at least partly in a spiral or helical formation along the outside or exterior of the probe needle. In some embodiments, the spiral part of the hollow channel extends from near the needle tip to near the probe body. In some embodiments, the dialysis membrance comprises a portion of a surface of the hollow channel and, in some embodiments, the dialysis membrane extends substantially the entire length of the hollow channel and comprises an outwardly facing surface of the hollow channel.

In one embodiment, the present invention comprises a microdialysis probe with a probe body, a probe needle for introduction into a tissue, an inlet line and an outlet line for a perfusion solution and a dialysis membrane, wherein a channel forms the outlet line and extends at least partly in a spiral about at least a portion of the probe needle on an external surface of the probe needle. In some embodiments, the inlet line also may be in the form of a channel that extends at least partly in a spiral about at least a portion of the external surface of the probe needle.

Accordingly, in one embodiment the present invention provides a microdialysis probe with a probe body and a probe needle for introduction into a tissue, comprising an inlet line and an outlet line for a perfusion solution, and a dialysis membrane, wherein at least the outlet line for the perfusion solution is formed by a channel which runs at least partly in a spiral formation or helical formation about the probe needle on an outer circumference of the probe needle. The spiral part of the channel preferably extends from a distal end portion of the probe needle, with the needle tip, to the probe body from which the probe needle emerges or by which the probe needle is carried. Substantially the entire channel for the outlet line is preferably provided with a dialysis membrane on its surface facing out or away from the probe needle. In this way, concentration equalization can take place along the entire length of the spiraling channel. Compared to the prior art devices and their straight lines, the spiral shape of the channel greatly increases the overall length of the outlet line for the perfusion solution, although the length of the needle remains unchanged. In this way, the dwell time of the perfusion solution inside the tissue is considerably lengthened, and its contact surface with the tissue environment is greatly increased.

In a microdialysis probe according to the present invention, a channel for the inlet line of the perfusion solution can run inside the probe needle, that is to say, through the spiral channel of the outlet line and as far as the tip of the probe needle. To form a probe needle of this kind, a cylindrical plastic element with a central bore can be provided, for example, said element having a bore which leads to the outer circumference surface and which opens into the spiral outlet line running around the plastic body.

In a preferred embodiment of the present invention, alongside a spiral hollow channel for the outlet line, another spiral hollow channel is provided for the inlet line for the perfusion solution. The two hollow channels of the inlet line and the outlet line run into one another in a reverse turn area at a distal end portion of the probe needle. In this case, a dialysis membrane is preferably provided both on the surface of the spiral inlet line facing out from the probe needle and also that of the spiral outlet line. In principle, it is possible to provide the dialysis membrane only in some areas of the probe needle. However, it is advantageous for the dialysis membrane to be arranged along the entire length of the hollow channels.

The dialysis membrane can, for example, be a hollow fiber which at the same time forms the hollow channel for the outlet line, and possibly also the inlet line. The use of a membrane hollow fiber has the advantage that, inside the tissue, no transitions between the material of the membrane and the material of the needle are required. In some embodiments, both the inlet line and the outlet line are preferably formed by a single membrane hollow fiber which makes a reverse turn in a distal end portion of the probe tip.

To form the probe needle, an elongate support body or a frame can be used on which the membrane fiber is arranged in the manner according to the invention. The inlet line in the form of the hollow fiber can be routed through the support body or frame and can emerge from the support body at the distal end portion of the support body and run back in a spiral formation around the support body to the probe housing. In some embodiments, it is preferable, however, for the inlet line also to run in a spiral formation around the outside of the probe needle or support body to the distal end portion of the needle. At the end portion, the hollow fiber membrane reverses and runs in a spiral formation, in the spaces between the inlet channel, back to the probe housing and thus forms the outlet line of the perfusion liquid. For this purpose, the probe needle is preferably formed by a cylindrical support body which, on its outer circumferential surface, has at least one recess which is open to the outside in the form of a depression and which runs in a spiral formation around at least part of the support body, but preferably along the entire length of said support body. In the case of a support body designed in this way, a membrane hollow fiber can be embedded in the depression. For this purpose, the depressions are preferably as deep as the external diameter of the membrane hollow fiber. In this way, the membrane hollow fiber is flush or even with the surface of the support body and is not exposed to a pressure exerted by the tissue. It is also possible, however, for the depression or depressions to be made less deep so that part of the membrane hollow fiber protrudes above the circumference surface of the support body, as a result of which the dialysis surface can be increased in size.

It is also possible for a dialysis membrane, in some embodiments in the form of a hollow fiber, to be tucked over or overlie a cylindrical support body with a spiral recess for the inlet and outlet lines, this dialysis membrane having an internal diameter approximately the same as the external diameter of the support body. At least those areas of the support body having the recess should be covered by the hollow fiber membrane. The hollow fiber membrane can, for example, be secured on the circumference surfaces of the support body which lie between the depressions. For this purpose, it is possible to use a suitable adhesive agent or other suitable method of attachment. The space between the tucked-over hollow fiber and the recess then forms the hollow channel at least for the inlet line for the perfusion solution, but preferably also for the outlet line for the perfusion solution. If the membrane hollow fiber is closed off in an area of the tip, that is to say, if it forms a kind of membrane sock, then, in this embodiment too, there are no transitions between the material of the membrane and the material of the probe needle inside the tissue.

In a further embodiment of a microdialysis probe according to the present invention the probe comprises a support body, which may be generally cylindrical, with a spiral recess or depressions, and a dialysis membrane in the form of a membrane layer or a membrane sheet is wound about the outer circumference of the support body. The abutting edges of the membrane layer are sealed tight, and the membrane layer is secured in the areas between the recess on the circumference surface of the support body. In this way, the hollow channels for the outlet line and inlet line of the perfusion solution are again obtained between the membrane layer and the recess (or recesses). In the last two embodiments described, the dialysis surface corresponds to the width of one recess times the length of the spiral depression. The perfusion solution can make contact with the tissue environment along the entire length of the probe needle inside the tissue.

When applying the dialysis membrane, it must be generally noted that it swells in a moist environment and its surface thus increases in size. This must be taken into account particularly if the membrane is secured across relatively large surface areas or if its diameter has to be adapted to the diameter of the support body.

In one embodiment in which both the inlet line and the outlet line run in a spiral formation about the probe needle, this forms a kind of double helix. The pitch of the spiral may be adapted to a desired flow velocity or to a desired dwell time of the perfusion solution in the tissue. A support body which forms the probe needle can, for example, be made of various plastics such as liquid-crystalline polymers, polybutylene terephthalate PBT, or also of PE or PET. Such materials can be worked by injection molding, for example. During the actual production of a cylindrical blank for the support body, depressions for the inlet and outlet lines can be formed in the blank, or they can be provided in the blank at a later stage by means of finishing work such as milling, cutting or etching. The area forming the distal end portion of such a cylindrical support body or frame is generally cut obliquely in order to form a tip for introduction into a tissue. The distal end portion of the support body is preferably beveled in such a way that the user experiences minimal pain and the tissue environment is minimally changed, such as is described, for example, in the patent application entitled "Injection needle tip" owned by the owner of the present application and bearing the same application date.

The probe needle of the microdialysis probe can be designed to pierce the skin. However, it is also possible to use an insertion aid for the probe needle. This is especially advantageous when wide areas of the membrane are arranged unprotected on the surface of the support body.

According to the present invention, it is in principle also possible to provide several spiraling inlet lines and/or outlet lines alongside or adjacent to one another on the outer circumference of the probe needle.

With a microdialysis probe having a design according to the invention, the path along which the perfusion solution is in contact with the tissue environment is lengthened, without having to make the probe needle longer. Conversely, it is possible to produce the same length of line, but on a shorter probe needle. This makes a microdialysis probe more comfortable for the user. Since, compared to an outlet line taking up the entire diameter of the probe needle, the lines according to the invention have a relatively small diameter, the ratio of surface to volume is improved, with the result that more perfusion liquid can come into contact with an outside surface of the dialysis membrane and, consequently, with the tissue environment.

BRIEF DESCRIPTION OF THE DRAWINGS

The invention is explained in more detail on the basis of illustrative embodiments, which are to be understood as non-limiting, and with reference to the accompanying drawings, in which.

DETAILED DESCRIPTION

Figure 1:
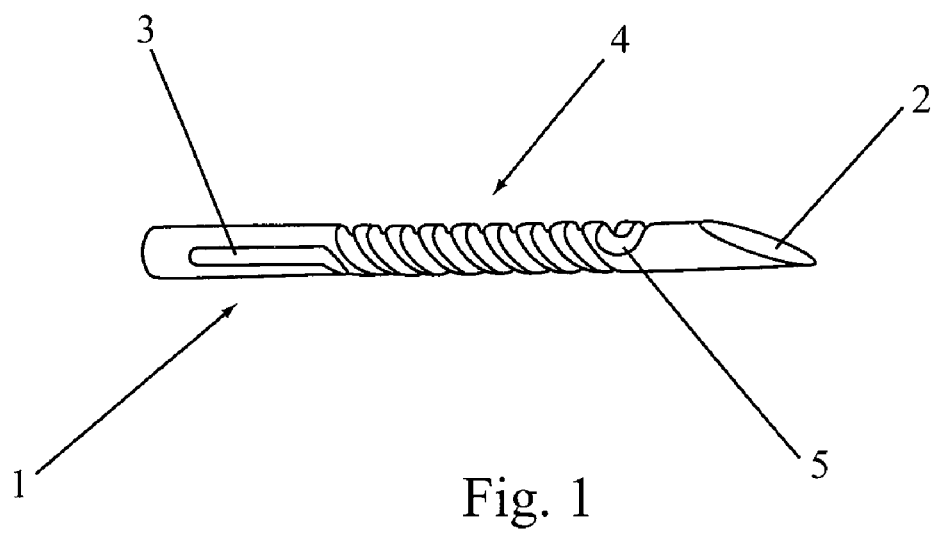
FIG. 1 shows a perspective view of one embodiment of a probe needle according to the present invention with a spiral inlet and outlet line.

In FIG. 1, a cylindrical support body 1 or frame is shown which forms a probe needle for a microdialysis probe. In a starting area of the support body inserted into a probe body, a recess or depression 3 begins which initially runs in the longitudinal direction of the support body 1, on the outer surface thereof. In a middle area 4 of the support body, the depression 3 merges into a spiral course. The spiral course extends to just before a distal end portion 2 of the support body 1 and forms, to that point, the depression for an inlet line for a perfusion solution. Before the distal end portion 2, the depression 3 makes a reverse turn 5 and extends from there in a spiral formation between the first spiral course for the inlet line and back to the starting area of the support body 1, thereby forming the depression for the outlet line for the perfusion liquid. In this way, two interlaced spiral courses are obtained, that is to say, in a kind of double helix configuration.

Figure 1A:
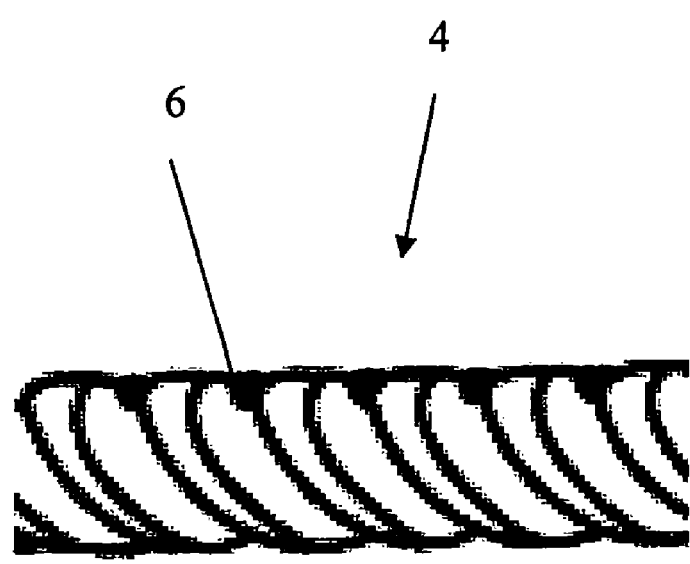
FIG. 1a shows a cut away view of the middle area of the support body of FIG. 1.

A membrane hollow fiber 6 (FIG. 1a), for example, can then be introduced into the course of the recess or depression 3, the membrane hollow fiber 6 following the course of the depression, from a starting area of the support body 1 along the depression 3 through the area 4 and via the reverse turn or deflection 5 to the distal end portion 2 of the support body 1 and then back through the spiral area 4 to the starting area of the support body 1. It is also possible, as has been described above, for a membrane hollow fiber with an internal diameter corresponding approximately to the external diameter of the support body 1 to be tacked over the support body 1 and secured in the intermediate spaces of the surface between the depressions 3, in which case the inlet and outlet lines are formed by the depression closed off by the membrane. Finally, it is likewise possible, as has been described above, for a membrane layer or a membrane sheet to be wound around the support body 1 and connected at a seam. The support body 1 with the dialysis membrane applied to it then forms the totality of the probe needle and is inserted into a probe body from which the perfusion solution is conveyed into/withdrawn from the inlet/outlet line.

Figure 2:
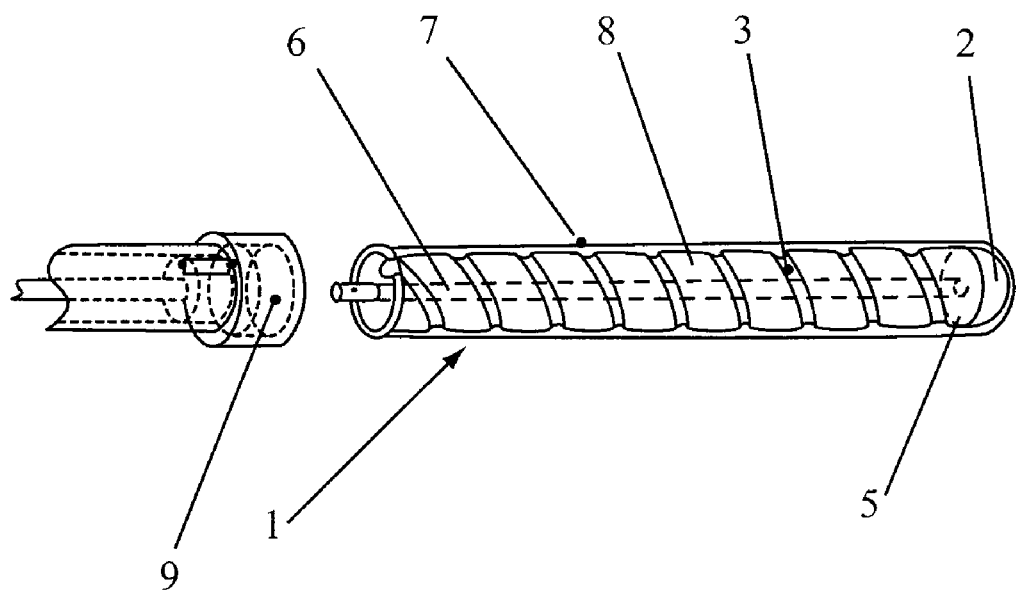
FIG. 2 shows a perspective view of a second embodiment of the present invention with a spiral outlet line and a rectilinear inlet line.

FIG. 2 shows a further embodiment of a microdialysis probe according to the invention with a cylindrical support body 1 which likewise has a spiral recess or depression 3 on its outer surface. This depression is provided for the outlet line of the perfusion solution. As the inlet line of the perfusion solution, a rectilinear hollow channel 6 is provided in a middle area of the support body 1 along the longitudinal axis of the support body, which hollow channel 6 extends from a starting area of the support body 1 to just before the distal end portion 2 of the support body. Just before the end portion 2, the hollow channel 6 is deflected in the direction of the outer circumference surface of the support body 1 so that it emerges from the outer circumference surface and forms the reverse turn 5. The outlet opening of the rectilinear hollow channel opens out into the spiral depression 3. In this way, a continuous hollow channel can, on the one hand, form the inlet line running from a starting area of the support body to its distal end portion 2 and, on the other hand, can form the outer spiraling outlet line back to the starting area of the support body 1.

In the illustrative embodiment shown in FIG. 2, a membrane hollow fiber 7 closed at the tip 1 and in the form of a membrane sock is arranged or wrapped over the support body 1. The membrane hollow fiber has an internal diameter slightly greater than the external diameter of the support body 1. The membrane hollow fiber 7 is secured in the intermediate areas 8 between the spiral course of the depression on the support body 1, as a result of which a hollow channel for the outlet line of the perfusion solution is formed between the membrane hollow fiber and the support body. In the example shown, the support body 1 is substantially completely enclosed or enveloped by the dialysis membrane. When such a probe needle is inserted, there are no transition points between the material of the membrane and the material of the support body within the tissue.

The probe needle made up of the support body 1 and membrane hollow fiber 7 is attached to a probe body 9 from which the inlet line is supplied with perfusion solution and into which the perfusion solution is returned via the outlet line after the concentration equalization.

In principle, it is also possible to choose, for the probe tip, a support body which has no depressions for forming the lines or for receiving a membrane hollow fiber. A hollow fiber membrane can be wound in a spiral formation around a smooth cylindrical support body of this kind and can be secured at certain intervals to the support body by means of a suitable adhesive agent or other suitable attachment method. When a probe needle of this kind is located in the tissue, the pressure of the perfusion solution within the lines must be great enough to withstand the external pressure exerted by the tissue and thus ensure that the line is not closed.

To configure a dialysis membrane in the spiral fashion described here, it is possible, for example, to employ a method as described in the patent application entitled "Microdialysis probe and method for the production thereof," the disclosure of which is incorporated herein by reference, and which is owned by the owners of the present application and bears the same application date. In said method, the dialysis membrane first lies on a shaping means and is brought into a predetermined shape by bending or forming the shaping means. An adhesive agent, such as adhesive cement or glue, is then applied at least partially to a bending point of the dialysis membrane, so that the membrane is maintained in the predetermined shape. After the adhesive agent has been applied, the shaping means is removed from the dialysis membrane. The shaping means can be a filament which is pulled through the hollow fiber membrane. The shape is defined by the spiral course of the microdialysis membrane according to the present invention.

The invention has been described by way of illustration on the basis of exemplary embodiments; the embodiments shown and described are not intended to limit the scope of the invention, and modifications and refinements are to be considered as belonging to the invention.

What is claimed is:

1. A microdialysis probe comprising:
a support body with a generally cylindrical shape having a spiral recess extending along a length of the outer circumference of the support body, wherein a distal end of the support body forms an obliquely cut needle tip for insertion into a tissue;
a dialysis membrane comprising a hollow fiber received in the spiral recess;
wherein the dialysis membrane forms a first hollow channel that defines an inlet path for carrying a perfusion solution in a distal direction;
wherein the dialysis membrane further forms a second hollow channel that defines an outlet path for carrying the perfusion solution in a proximal direction; and
wherein the support body further includes a recessed reverse turn area that joins the inlet path to the outlet path.

2. The microdialysis probe of claim 1, wherein the inlet path and the outlet path are formed by a single hollow fiber membrane.

3. The microdialysis probe of claim 1, wherein the hollow fiber is positioned in the spiral recess such that an external surface of the hollow fiber is substantially flush with the outer circumference of the support body.

4. The microdialysis probe of claim 1, wherein the hollow fiber is positioned in the spiral recess such that an external surface of the hollow fiber is protrudes above the outer circumference of the support body.

5. The microdialysis probe of claim 1, wherein the spiral recess extends along substantially the entire length of the outer circumference of the support body.

* * * * *